United States Patent
Zoellner (10) Patent No.: US 9,954,182 B2
(45) Date of Patent: Apr. 24, 2018

(54) SEMICONDUCTING MATERIAL COMPRISING A PHOSPHEPINE MATRIX COMPOUND

(71) Applicant: Novaled GmbH, Dresden (DE)

(72) Inventor: Mike Zoellner, Dresden (DE)

(73) Assignee: NOVALED GMBH, Dresden (DE)

( * ) Notice: Subject to any disclaimer, the term of this patent is extended or adjusted under 35 U.S.C. 154(b) by 72 days.

(21) Appl. No.: 15/107,261

(22) PCT Filed: Dec. 23, 2014

(86) PCT No.: PCT/EP2014/079180
§ 371 (c)(1),
(2) Date: Jun. 22, 2016

(87) PCT Pub. No.: WO2015/197225
PCT Pub. Date: Jul. 2, 2015

(65) Prior Publication Data
US 2016/0336516 A1 Nov. 17, 2016

(30) Foreign Application Priority Data
Dec. 23, 2013 (EP) .................................. 13199361

(51) Int. Cl.
| H01L 51/50 | (2006.01) |
| H01L 51/00 | (2006.01) |
| C07F 9/53 | (2006.01) |
| C07F 9/58 | (2006.01) |
| C07F 9/6568 | (2006.01) |

(52) U.S. Cl.
CPC ........ H01L 51/0071 (2013.01); C07F 9/5325 (2013.01); C07F 9/5329 (2013.01); C07F 9/587 (2013.01); C07F 9/6568 (2013.01); C07F 9/65685 (2013.01); H01L 51/005 (2013.01); H01L 51/0077 (2013.01); H01L 51/5076 (2013.01); H01L 51/5092 (2013.01)

(58) Field of Classification Search
CPC ............... H01L 51/0071; H01L 51/005; H01L 51/0077; H01L 51/5076; H01L 51/5092; C07F 9/535; C07F 9/5329; C07F 9/587; C07F 9/6568; C07F 9/65685
USPC ........................................................ 428/690
See application file for complete search history.

(56) References Cited

U.S. PATENT DOCUMENTS

| 9,806,266 B2 | 10/2017 | Kanitz et al. |
| 2012/0097934 A1* | 4/2012 | Sung ................... H01L 51/0054 257/40 |
| 2013/0231424 A1 | 9/2013 | Anada et al. |
| 2014/0249308 A1* | 9/2014 | Parham ................ C07D 471/06 544/215 |

OTHER PUBLICATIONS

PCT International Search Report and Written Opinion for PCT Application No. PCt/EP2014/079180 dated Feb. 24, 2015.
European Search Report for EP Application No. 13199361.0 dated Oct. 31, 2014.
Taiwanese Office Action for TW Application No. 103145093 dated Jan. 25, 2018 (3 pages) (English translation).

* cited by examiner

*Primary Examiner* — Jayne L Mershon
(74) *Attorney, Agent, or Firm* — Eversheds Sutherland (US) LLP (57) ABSTRACT

The invention is directed to a use of a compound comprising at least one phosphepine ring as matrix material in semi-conducting materials, the semiconducting material as well as electronic devices. The phosphepine ring matrix material may be doped by a lithium complex.

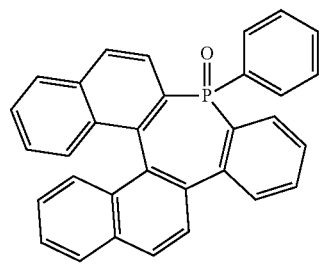

(E1)

14 Claims, 2 Drawing Sheets

SEMICONDUCTING MATERIAL COMPRISING A PHOSPHEPINE MATRIX COMPOUND

CROSS REFERENCE TO RELATED APPLICATIONS

This application is a U.S. national stage application of PCT/EP2014/079180, filed Dec. 23, 2014, which claims priority to European Application No. 13199361.0, filed Dec. 23, 2013. The contents of these applications are hereby incorporated by reference.

The present invention concerns use of organic compounds comprising a phosphepine ring as and/or in semiconducting materials, semiconducting materials with improved electrical properties that comprise a phosphepine matrix compound and electronic device utilizing phosphepine compounds and/or improved electrical properties of the inventive semiconducting material.

I. BACKGROUND OF THE INVENTION

Among the electronic devices comprising at least a part based on material provided by organic chemistry, organic light emitting diodes (OLEDs) have a prominent position. Since the demonstration of efficient OLEDs by Tang et al. in 1987 (C. W. Tang et al., Appl. Phys. Lett. 51 (12), 913 (1987)), OLEDs developed from promising candidates to high-end commercial displays. An OLED comprises a sequence of thin layers substantially made of organic materials. The layers typically have a thickness in the range of 1 nm to 5 μm. The layers are usually formed either by means of vacuum deposition or from a solution, for example by means of spin coating or jet printing.

OLEDs emit light after the injection of charge carriers in the form of electrons from the cathode and in form of holes from the anode into organic layers arranged in between. The charge carrier injection is effected on the basis of an applied external voltage, the subsequent formation of excitons in a light emitting zone and the radiative recombination of those excitons. At least one of the electrodes is transparent or semitransparent, in the majority of cases in the form of a transparent oxide, such as indium tin oxide (ITO), or a thin metal layer.

Some phosphepine compounds are known in the scientific literature, e.g. formation of 11-phenylbenzo[b]dinaphtho-[2,1-d:1',2'-f]phosphepine-11-oxide (CAS 597578-28-6) by an intramolecular substitution reaction was reported in Bull. Chem. Soc. Jpn., 76, 1233-1244 (2003).

It is an objective of the invention to overcome the drawbacks of the prior art and to find compounds which can improve the performance of organic electronic devices. Specifically, the sought compounds shall be successfully embedded in electrically doped semiconducting materials for use in electronic devices. The inventive semiconducting materials shall afford devices with better characteristics, especially with low voltage and higher efficiency, more specifically, OLEDs with higher power efficiency, even more specifically, OLEDs having satisfactory efficiency and long lifetime.

II. SUMMARY OF THE INVENTION

The object is achieved by use of a compound comprising at least one phosphepine ring in semiconducting material.

Preferably, the compound comprising at least one phosphepine ring further comprises at least one phosphine oxide group.

More preferably, the phosphepine ring is a phosphepine-1-oxide ring. Most preferably, the compound comprising at least one phosphepine ring is used as a charge transporting matrix.

The object is further achieved by semiconducting material comprising at least one matrix compound, wherein the matrix compound comprises at least one phosphepine ring. Optionally, the semiconducting material further comprises at least one dopant. In one of preferred embodiments, the dopant is an electrical dopant. Also preferably, the phosphepine ring is a phosphepine-1-oxide ring. In another preferred embodiment, the electrical dopant is n-dopant. Also preferably, the dopant is a metal, a metal salt or a metal complex.

In a further preferred embodiment, the metal complex is a compound comprising at least one ligand attached to the metal atom through at least one oxygen atom and through at least one nitrogen atom, and the metal, oxygen and nitrogen atom are comprised in a 5-, 6- or 7-membered ring. Example of such ligand is 8-hydroxyquinolinolato ligand.

In another preferred embodiment, the metal complex has formula (II)

(II)

wherein $A^1$ is a $C_6$-$C_{30}$ arylene or $C_2$-$C_{30}$ heteroarylene comprising at least one atom selected from O, S and N in an aromatic ring and each of $A^2$-$A^3$ is independently selected from a $C_6$-$C_{30}$ aryl and $C_2$-$C_{30}$ heteroaryl comprising at least one atom selected from O, S and N in an aromatic ring. Preferred example of $A^1$ is phenylene, preferred examples of $A^2$ and $A^3$ are phenyl and pyridyl.

The phosphepine compound has preferably formula (I):

wherein $R^1$, $R^2$ and $R^3$ are independently selected from
$C_1$-$C_{30}$-alkyl, $C_3$-$C_{30}$ cycloalkyl, $C_2$-$C_{30}$-heteroalkyl, $C_6$-$C_{30}$-aryl, $C_2$-$C_{30}$-heteroaryl, $C_1$-$C_m$-alkoxy, $C_3$-$C_{30}$-cycloalkyloxy, $C_6$-$C_{30}$-aryloxy, wherein
at least two of the substituents $R^1$, $R^2$ and $R^3$ are linked together the way that they form a phosphepine ring.

If not explicitly stated that a group or structural unit is unsubstituted, the given count of atoms (e.g., given count of carbon atoms) comprises also possible substituents.

Preferably, the semiconducting material comprising the dopant and the phosphepine matrix compound serves as an electron transporting material or as an electron injecting material.

It is preferred that the semiconducting material according to the invention comprises the dopant and the phosphepine matrix compound at least partly in form of a homogeneous mixture, wherein both components are molecularly dispersed in each other.

Another object the invention is achieved by an electronic device comprising at least one semiconducting material comprising a phosphepine matrix compound, preferably in form of an electronic device wherein the inventive semiconducting material comprising the phosphepine matrix compound forms at least one layer between a cathode and an anode.

Specifically, the second object of the invention is represented by an electronic device comprising at least one semiconducting layer comprising the doped semiconducting material according to the invention or consisting of it. More specifically, the semiconducting material according to the invention is used in the electronic device as an electron transporting layer, as an electron injecting layer, or as a layer having double electron transporting and hole blocking function.

Preferably, the electronic device is a light emitting device.

IV. DETAILED DESCRIPTION OF THE INVENTION

Device Architecture

Figure 1:
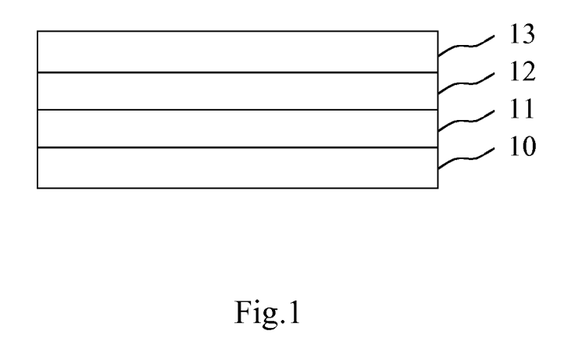
FIG. 1 shows a schematic illustration of a device in which the present invention can be incorporated.

FIG. 1 shows a stack of anode (10), organic semiconducting layer (11) comprising the light emitting layer, electron transporting layer (ETL) (12), and cathode (13). Other layers, can be inserted between those depicted, as explained herein.

Figure 2:
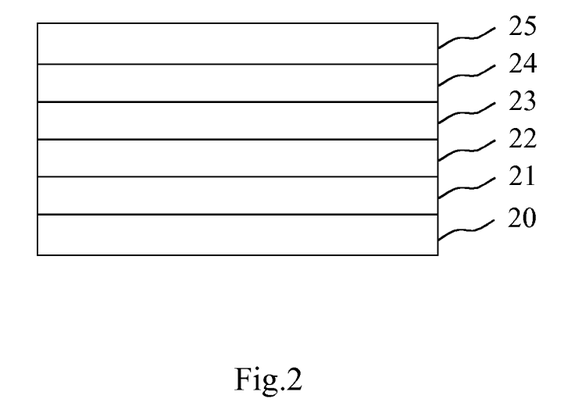
FIG. 2 shows a schematic illustration of a device in which the present invention can be incorporated.

FIG. 2 shows a stack of an anode (20), a hole injecting and transporting layer (21), a hole transporting layer (22) which can also aggregate the function of electron blocking, a light emitting layer (23), an ETL (24), and a cathode (25). Other layers can be inserted between those depicted, as explained herein.

The wording "device" comprises the organic light emitting diode.

Material Properties—Energy Levels

A method to determine the ionization potentials (IP) is the ultraviolet photo spectroscopy (UPS). It is usual to measure the ionization potential for solid state materials; however, it is also possible to measure the IP in the gas phase. Both values are differentiated by their solid state effects, which are, for example the polarization energy of the holes that are created during the photo ionization process. A typical value for the polarization energy is approximately 1 eV, but larger discrepancies of the values can also occur. The IP is related to beginning of the photoemission spectra in the region of the large kinetic energy of the photoelectrons, i.e. the energy of the most weakly bounded electrons. A related method to UPS, the inverted photo electron spectroscopy (IPES) can be used to determine the electron affinity (EA). However, this method is less common. Electrochemical measurements in solution are an alternative to the determination of solid state oxidation ($E_{ox}$) and reduction ($E_{red}$) potential. An adequate method is for example the cyclo-voltammetry. A simple rule is used very often for the conversion of red/ox potentials into electron affinities and ionization potential: IP=4.8 eV+e*$E_{ox}$ (vs. ferrocenium/ferrocene (Fc$^+$/Fc)) and EA=4.8 eV+e*$E_{red}$ (vs. Fc$^+$/Fc) respectively (see B. W. D'Andrade, Org. Electron. 6, 11-20 (2005)). Processes are known for the correction of the electrochemical potentials in the case other reference electrodes or other redox pairs are used (see A. J. Bard, L. R. Faulkner, Electrochemical Methods: Fundamentals and Applications", Wiley, 2. Ausgabe 2000). The information about the influence of the solution used can be found in N. G. Connelly et al., Chem. Rev. 96, 877 (1996). It is usual, even if not exactly correct to use the terms, "energy of the HOMO" $E_{(HOMO)}$ and "energy of the LUMO" $E_{(LUMO)}$ respectively as synonyms for the ionization energy and electron affinity (Koopmans theorem). It has to be taken in consideration, that the ionization potentials and the electron affinities are given in such a way that a larger value represents a stronger binding of a released or respectively of an absorbed electron. The energy scale of the frontier molecular orbitals (HOMO, LUMO) is opposed to this. Therefore, in a rough approximation, is valid: IP=-$E_{(HOMO)}$ and EA=$E_{(LUMO)}$. The given potentials correspond to the solid-state potentials.

Substrate

It can be flexible or rigid, transparent, opaque, reflective, or translucent. The substrate should be transparent or translucent if the light generated by the OLED is to be transmitted through the substrate (bottom emitting). The substrate may be opaque if the light generated by the OLED is to be emitted in the direction opposite of the substrate, the so called top-emitting type. The OLED can also be transparent. The substrate can be either arranged adjacent to the cathode or anode.

Electrodes

The electrodes are the anode and the cathode, they must provide a certain amount of conductivity, being preferentially conductors. Preferentially the "first electrode" is the cathode. At least one of the electrodes must be semitransparent or transparent to enable the light transmission to the outside of the device. Typical electrodes are layers or a stack of layer, comprising metal and/or transparent conductive oxide. Other possible electrodes are made of thin busbars (e.g. a thin metal grid) wherein the spaces between the busbars is filled (coated) with a transparent material with a certain conductivity, such as graphene, carbon nanotubes, doped organic semiconductors, etc.

In one mode, the anode is the electrode closest to the substrate, which is called non-inverted structure. In another mode, the cathode is the electrode closest to the substrate, which is called inverted structure.

Typical materials for the Anode are ITO and Ag. Typical materials for the cathode are Mg:Ag (10 vol. % of Mg), Ag, ITO, Al. Mixtures and multilayer are also possible.

Preferably, the cathode comprises a metal selected from Ag, Al, Mg, Ba, Ca, Yb, In, Zn, Sn, Sm, Bi, Eu, Li, more preferably from Al, Mg, Ca, Ba and even more preferably selected from Al or Mg. Preferred is also a cathode comprising an alloy of Mg and Ag.

Hole-Transporting Layer (HTL)

Is a layer comprising a large gap semiconductor responsible to transport holes from the anode or holes from a CGL to the light emitting layer (LEL). The HTL is comprised between the anode and the LEL or between the hole generating side of a CGL and the LEL. The HTL can be mixed with another material, for example a p-dopant, in which case it is said the HTL is p-doped. The HTL can be comprised by several layers, which can have different compositions. P-doping the HTL lowers its resistivity and avoids the respective power loss due to the otherwise high resistivity of the undoped semiconductor. The doped HTL can also be used as optical spacer, because it can be made very thick, up to 1000 nm or more without significant increase in resistivity.

Suitable hole transport materials (HTM) can be, for instance HTM from the diamine class, where a conjugated system is provided at least between the two diamine nitrogens. Examples are N4,N4'-di(naphthalen-1-yl)-N4,N4'-diphenyl-[1,1'-biphenyl]-4,4'-diamine (HTML), N4,N4, N4'', N4''-tetra([1,1'-biphenyl]-4-yl)-[1,1':4':4''-terphenyl]-4,4''-diamine (HTM2). The synthesis of diamines is well described in literature; many diamine HTMs are readily commercially available.

Hole-Injecting Layer (HIL)

Is a layer which facilitates the injection of holes from the anode or from the hole generating side of a CGL into an adjacent HTL. Typically the HIL is a very thin layer (<10 nm). The hole injection layer can be a pure layer of p-dopant and can be about 1 nm thick. When the HTL is doped, an HIL may not be necessary, since the injection function is already provided by the HTL.

Light-Emitting Layer (LEL)

The light emitting layer must comprise at least one emission material and can optionally comprise additional layers. If the LEL comprises a mixture of two or more materials the charge carrier injection can occur in different materials for instance in a material which is not the emitter, or the charge carrier injection can also occur directly into the emitter. Many different energy transfer processes can occur inside the LEL or adjacent LELs leading to different types of emission. For instance excitons can be formed in a host material and then be transferred as singlet or triplet excitons to an emitter material which can be singlet or triplet emitter which then emits light. A mixture of different types of emitter can be provided for higher efficiency. Mixed light can be realized by using emission from an emitter host and an emitter dopant.

Blocking layers can be used to improve the confinement of charge carriers in the LEL, these blocking layers are further explained in U.S. Pat. No. 7,074,500-B2.

Electron-Transporting Layer (ETL)

Is a layer comprising a large gap semiconductor responsible to transport electrons from the cathode or electrons from a CGL or EIL (see below) to the light emitting layer (LEL). The ETL is comprised between the cathode and the LEL or between the electron generating side of a CGL and the LEL. The ETL can be mixed with an electrical n-dopant, in which case it is said the ETL is n-doped. The ETL can be comprised by several layers, which can have different compositions. Electrical n-doping the ETL lowers its resistivity and/or improves its ability to inject electrons into an adjacent layer and avoids the respective power loss due to the otherwise high resistivity (and/or bad injection ability) of the undoped semiconductor. The doped ETL can also be used as optical spacer, because it can be made very thick, up to 1000 nm or more without significant increase in resistivity.

The present invention also employs a compound according to formula (I) in the ETL, which compound can be used in combination with other materials, in the whole layer or in a sub-layer of the ETL.

Hole blocking layers and electron blocking layers can be employed as usual.

In one mode of the invention the ETL comprises 2 layers, the first ETL (ETL1) and the second ETL (ETL2), ETL1 is closer to the LEL than the ETL2. Preferentially ETL1 comprises the compound according to formula 1, even more preferably consists only of material according to formula (I). Also preferably, ETL1 is closer to the substrate than ETL2.

Alternatively or in addition, the ETL2 comprises a compound according to formula (I). Preferably, the ETL2 is electrically doped.

Optionally ETL1 and ETL2 comprise the same compound according to formula (I).

Other layers with different functions can be included, and the device architecture can be adapted as known by the skilled in the art. For example, an Electron-Injecting Layer (EIL) can be used between the cathode and the ETL. Also the EIL can comprise the inventive matrix compounds of the present application.

Charge Generation Layer (CGL)

The OLED can comprise a CGL which can be used in conjunction with an electrode as inversion contact, or as connecting unit in stacked OLEDs. A CGL can have the most different configurations and names, examples are pn-junction, connecting unit, tunnel junction, etc. Best examples are pn junctions as disclosed in US 2009/0045728 A1, US 2010/0288362 A1. Metal layers and or insulating layers can also be used.

Stacked OLEDs

When the OLED comprises two or more LELs separated by CGLs, the OLED is named a stacked OLED, otherwise it is named a single unit OLED. The group of layers between two closest CGLs or between one of the electrodes and the closest CGL is named a electroluminescent unit (ELU). Therefore a stacked OLED can be described as anode/$ELU_1$/$\{CGL_X/ELU_{1+X}\}_X$/cathode, wherein x is a positive integer and each $CGL_X$ or each $ELU_{1+X}$ can be equal or different. The CGL can also be formed by the adjacent layers of two ELUs as disclosed in US2009/0009072 A1. Further stacked OLEDs are explained e.g. in US 2009/0045728 A1, US 2010/0288362 A1, and references therein.

Deposition of Organic Layers

Any organic semiconducting layers of the inventive display can be deposited by known techniques, such as vacuum thermal evaporation (VTE), organic vapour phase deposition, laser induced thermal transfer, spin coating, blade coating, slot dye coating, inkjet printing, etc. A preferred method for preparing the OLED according to the invention is vacuum thermal evaporation.

Preferably, the ETL is formed by evaporation. When using an additional material in the ETL, it is preferred that the ETL is formed by co-evaporation of the electron transporting matrix (ETM) and the additional material. The additional material may be mixed homogeneously in the ETL. In one mode of the invention, the additional material has a concentration variation in the ETL, wherein the concentration changes in the direction of the thickness of the stack of layers. It is also foreseen that the ETL is structured in sub-layers, wherein some but not all of these sub-layers comprise the additional material.

Electrical Doping

The present invention can be used in addition or in combination with electrical doping of organic semiconducting layers.

The most reliable and at the same time efficient OLEDs are OLEDs comprising electrically doped layers. Generally, the electrical doping means improving of electrical properties, especially the conductivity and/or injection ability of a doped layer in comparison with neat charge-transporting matrix without a dopant. In the narrower sense, which is usually called redox doping or charge transfer doping, hole transport layers are doped with a suitable acceptor material (p-doping) or electron transport layers with a donor material (n-doping), respectively. Through redox doping, the density of charge carriers in organic solids (and therefore the conductivity) can be increased substantially. In other words, the redox doping increases the density of charge carriers of a semiconducting matrix in comparison with the charge carrier density of the undoped matrix. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

US2008227979 discloses in detail the charge-transfer doping of organic transport materials, with inorganic and with organic dopants. Basically, an effective electron transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of known redox doped hole transport materials are: copperphthalocyanine (CuPc), which HOMO level is approximately −5.2 eV, doped with tetrafluoro-tetracyanocptinonedimethane (F4TCNQ), which LUMO level is about −5.2 eV; zincphthalocyanine (ZnPc) (HOMO=−5.2 eV) doped with F4TCNQ; a-NPD Bis(naphthalen-1-yl)-N,N'-bis(phenyl)-benzidine) doped with F4TCNQ. a-NPD doped with 2,2'-(perfluoronaphthalene-2, 6-diylidene) dimalononitrile (PD1). a-NPD doped with 2,2', 2''-(cyclopropane-1,2,3-triylidene)tris(2-(p-cyanotetrafluorophenyl)acetonitrile) (PD2). All p-doping in the device examples of the present application was done with 8 wt. % of PD2.

Typical examples of known redox doped electron transport materials are: fullerene C60 doped with acridine orange base (AOB); perylene-3,4,9,10-tetracarboxylic-3,4,9,10-di-anhydride (PTCDA) doped with leuco crystal violet; 2,9-di (phenanthren-9-yl)-4,7-diphenyl-1,10-phenanthroline doped with tetrakis (1,3,4,6,7,8-hexahydro-2H-pyrimido[1,2-a] pyrimidinato) ditungsten(II) (W$_2$(hpp)$_4$); naphthalene tetracarboxylic acid di-anhydride (NTCDA) doped with 3,6-bis-(dimethyl amino)-acridine; NTCDA doped with bis (ethylene-dithio) tetrathiafulvalene (BEDT-TTF).

It was found that phosphepine compounds comprising at least one phosphine oxide group may be successfully converted in highly conductive electron transport semiconducting materials by electrical doping with metals. Such electrically doped semiconducting material can be easily prepared by co-deposition of metal vapours with the vapour of a phosphepine compound comprising at least one phosphine oxide group on a solid substrate. Besides alkali metals, this electrical doping works very well also with other metals having significantly higher ionization potentials and lower reductive power. Their lower reactivity is thus especially advantageous for easy handling in industrial manufacturing processes. Particularly advantageous n-dopants for phosphepine electron transport matrices comprising at least one phosphine oxide group are alkaline earth metals and rare earth metals. Typical representatives of these groups are magnesium and ytterbium, which are particularly advantageous due their favourable vaporization temperatures under high vacuum conditions, well-fitting with vaporization temperatures of typical electron transport matrix compounds.

It was further found that classical redox dopants with high reduction strength, expressed as a highly negative redox potential measured by cyclic voltammetry (CV) in THF vs. Fc+/Fc standard, may be in phosphepine electron transport matrices successfully replaced with metal salts having no pronounced reductive properties. True mechanism how these compounds, sometimes called "electrically doping additives", contribute to the lowering of the voltage in electronic devices, is not yet known.

Typical known representative of such metal salts is lithium 8-hydroxyquinolinolate (LiQ) represented by the formula D1

Many other similar lithium complexes comprising five- or six-membered chelate ring wherein Li is coordinated to an oxygen and a nitrogen atom are known and were used or proposed as electrical dopants for organic electron transporting semiconducting materials.

As already stated above, the doped semiconducting material according to one of preferred embodiments comprises lithium salt having general formula (II)

Formula (II)

wherein $A^1$ is a $C_6$-$C_{30}$ arylene or $C_2$-$C_{30}$ heteroarylene comprising at least one atom selected from O, S and N in an aromatic ring and each of $A^2$-$A^3$ is independently selected from a $C_6$-$C_{30}$ aryl and $C_2$-$C_{30}$ heteroaryl comprising at least one atom selected from O, S and N in an aromatic ring, wherein any aryl, arylene, heteroaryl and/or heteroarylene may be independently unsubstituted or substituted with groups selected from hydrocarbon groups comprising only C and H, alkoxy, aryloxy and lithiumoxy, provided that the given C count in an aryl, heteroaryl, arylene or heteroarylene group includes also all substituents present on the said group.

It is to be understood that the term substituted or unsubstituted arylene stands for a divalent radical derived from substituted or unsubstituted arene, wherein the both adjacent structural moieties (in formula (II), the OLi group and the diaryl phosphine oxide group) are attached directly to an aromatic ring of the arylene group. Similarly, the term substituted or unsubstituted heteroarylene stands for a divalent radical derived from substituted or unsubstituted heteroarene, wherein the both adjacent structural moieties (in formula (II), the OLi group and the diaryl phosphine oxide group) are attached directly to an aromatic ring of the heteroarylene group. Example compounds of this class of dopants are represented by structures D2 and D3

Compound D2 was disclosed in the application PCT/EP2012/074127, published as WO2013/079678 A1, and compound D3 in the application EP13170862.

The lithium complex (II) works in the inventive semiconducting material as an electrical dopant, whereas the phosphepine compound has the function of a charge transporting matrix.

Phosphepine Matrix Compound

The phosphepine ring is a specific example of a conjugated system of delocalized electrons. The phosphepine compound used in the invention comprises at least one conjugated system with at least 6 delocalized electrons, preferably with at least 10 delocalized electrons, more preferably with at least 14 delocalized electrons. In another preferred embodiment, the phosphepine compound comprises at least two conjugated system of delocalized electrons linked with the phosphorus atom.

Examples of conjugated systems of delocalized electrons are systems of alternating pi- and sigma bonds, wherein, optionally, one or more two-atom structural units having the pi-bond between its atoms can be replaced by an atom bearing at least one lone electron pair, typically by a divalent O or S atom. Alternatively or in an addition, the system of alternating pi- and sigma bonds may embed one or more isolated boron atoms having only six valence electrons and one vacant orbital. Preferably, the conjugated system of delocalized electrons comprises at least one aromatic ring adhering to the nickel rule. More preferably, the conjugated system of delocalized electrons comprises a condensed aromatic skeleton comprising at least 10 delocalized electrons, e.g. a naphthalene, anthracene, phenanthrene, pyrene, benzofurane or benzothiophene skeleton. Also preferably, the conjugated system of delocalized electrons may consist of at least two directly attached aromatic rings, the simplest examples of such systems being biphenyl, bithienyl, phenylthiophene, furylthiophene and like.

In one embodiment of the invention, the phosphepine ring comprises at least one polycyclic aromatic or a polycyclic heteroaromatic system of delocalized electrons. The polycyclic (hetero)aromatic system may be directly attached to the phosphorus atom, or may be separated from the phosphorus atom by a double bond or by a monocyclic aromatic or heteroaromatic ring.

In one preferred embodiment of the invention, the lowest unoccupied molecular orbital (LUMO) of the phosphepine matrix compound is localized mainly on a polycyclic aromatic or heteroaromatic ring system. As a rule of thumb, it can be supposed that the presence of at least 10 fully delocalized electrons in the conjugated (hetero)aromatic system makes the lowest unoccupied molecular orbital of the whole phosphepine matrix compound localized mainly on the polycyclic (hetero)aromatic ring system.

More specifically, the localization of a frontier orbital like LUMO in the molecule can be assigned by a skilled person to that part of the molecule which contains the largest conjugated pi-electron system. In case that two or more pi-electron systems with the same extent (given by the number of pi electrons in conjugation) occur in the molecule, the lowest energy can be assigned to the system linked with strongest electron withdrawing groups and/or weakest electron donating groups. The electron withdrawing and/or electron accepting effects of various substituents are commensurate to experimentally accessible parameters like Hammet or Taft constants which are tabulated for large number of substituents most frequently occurring in aromatic or heteroaromatic organic compounds. In most cases, the above mentioned parameters are sufficient for a reliable LUMO localization, because the overall effect of more substituents attached to the same aromatic system is additive. In case of uncertainty, the ultimate method for the correct LUMO localization in the molecule is quantum chemical calculation. Reliable results with relatively low demand for computational capacity provide for example the methods based on density functional theory (DFT methods).

It is desirable that the LUMO level of the phosphepine matrix compound, measured as a redox potential by cyclic voltammetry (CV) in tetrahydrofuran (THF) against ferrocenium/ferrocene redox couple as a reference, is in the range −1.8--−3.1 V. It is preferred that the energy of this LUMO is in the range −2.0--−2.9 V, more preferably in the range −2.15--−2.75 V, even more preferably in the range −2.25--−2.6 V. Modern quantum chemical methods allow also a reliable estimation of relative LUMO energies for different molecules. The computed relative values can be recalculated to absolute scale corresponding to the electrochemical potentials measured in a concrete CV experimental setting, if the calculated value is compared with the value measured for the same compound and the obtained difference is taken into account as a correction for the values calculated for other compounds.

An example of phosphepine matrix compound of the present invention is compound E1

V. ADVANTAGEOUS EFFECT OF THE INVENTION

The favourable effects of the inventive electron-transporting matrix materials are shown in comparison with comparative devices comprising instead of the inventive compounds electron transporting matrices which lack the inventive combination of phosphine oxide group and electron transporting unit with a phenylene spacer. Comparative compounds C1-C4 characterized in more detail in the examples are referred to.

Table 1 shows the performance of inventive and comparative compounds in bottom emission structured OLEDs, described in detail in examples 1, with respect to voltage (U) and quantum efficiency (Qeff). Additionally, the values of the CIE 1931 coordinate y are given as a measure of similar spectral distribution of luminance in the compared devices and values of the average time necessary for the 3% change in the initial luminance (LT97) at the room temperature are reported as another parameter for the compound performance.

11-Phenylbenzo[b]dinaphtho[2,1-d:1',2'-f]phosphepine-11-oxide (E1)

TABLE 1

| | | D1 doped | | | | | D2 doped | | | |
|---|---|---|---|---|---|---|---|---|---|---|
| Code | LUMO (V) | U (V) | Qeff | Q/U | CIEy | LT97 (h) | U (V) | Qeff | Q/U | CIEy | LT97 (h) |
| E1 | −2.62 | 4.9 | 5.4 | 1.10 | | 375 | 4.9 | 6.5 | 1.33 | 0.095 | 215 |
| C1 | −2.27 | 4.9 | 5.5 | 1.12 | 0.094 | 510 | 4.8 | 6.9 | 1.44 | 0.092 | 150 |
| C2 | −2.19 | 4.7 | 4.9 | 1.04 | 0.096 | 266 | 5.0 | 5.6 | 1.12 | 0.098 | 226 |
| C3 | −2.24 | 4.1 | 6.5 | 1.59 | 0.103 | 51 | 4.2 | 7.1 | 1.69 | 0.103 | 70 |
| C4 | −2.69 | 6.7 | 4.0 | 0.60 | 0.105 | 0.2 | 6.6 | 6.5 | 0.98 | 0.100 | 1.8 |

I. EXAMPLES

General Remarks for Synthesis:

All reactions with moisture- and/or air-sensitive agents were carried out under argon atmosphere using oven dried glassware. Starting materials were used as purchased without further purification. Materials, which were used to build OLEDs, were sublimed by gradient sublimation to achieve highest purity.

Analytics:

Final materials were characterized by mass spectrometry (MS) and proton magnetic resonance ($^1$H-NMR). NMR samples were dissolved in $CD_2Cl_2$ unless otherwise stated. Melting points (mp) were determined by differential scanning calorimetry (DSC). Peak temperatures are reported. If gas chromatography-mass spectrometry (GC-MS) or high performance liquid chromatography (HPLC) with electrospray ionization mass spectroscopy (ESI-MS) were used for the product characterization, only the mass/charge (m/z) ratios for the molecular peak are reported. For brominated intermediates, the corresponding isotopic multiplet is reported.

Step 1

[1,1'-Binaphthalen]-2,2'-diylbis(diphenylphosphine oxide) (C4)

(1,1'-Binaphthalen-2,2'-diyl)bis(diphenylphosphine) (124.00 g, 199.14 mmol, 1 eq) was suspended in dichloromethane (1.75 L) and cooled to 5° C. with an ice bath. Hydrogen peroxide (61.0 mL, 597.4 mmol, 3 eq) was added slowly to the suspension within 1 h. The ice bath was removed and the suspension was stirred overnight at room temperature. The mixture was washed in portions with brine (2×150 mL per 600 mL reaction solution). The organic phase was collected, dried over sodium sulphate, filtered and the solvent was evaporated. The crude product was suspended in a mixture of n-hexane and DCM (400 mL, 95:5, vol:vol), filtered, washed with n-hexane and dried under vacuum overnight.
Yield: 125.07 g (96%), white powder.
Purity: HPLC: 99.5%
Melting point: 302° C. (from DSC (peak at 10 K/min))

Step 2

11-Phenylbenzo[b]dinaphtho-[2,1-d:1',2'-f]phosphepine-11-oxide) (E1)

[1,1'-Binaphthalene]-2,2'-diylbis(diphenylphosphine oxide, (C4)) (65.47 g, 100.00 mmol, 1 eq) was suspended in dry THF (655 mL) under argon atmosphere. After cooling the suspension to 0° C. with an ice bath, the LDA-solution (100.00 mL, 200.00 mmol, 2 eq) was added dropwise within 40 min. The suspension was stirred for another 30 min at 0° C., then the ice bath was removed and stirring was continued for 2.5 h at room temperature. After quenching the reaction by the addition of HCl (13 mL, 2 M), a white precipitate was formed. The suspension was stirred for additional 30 min and then the precipitate was collected by filtration. The crude product was washed with n-hexane (3×100 mL) and water (2×100 mL). Then the solid material was suspended in water (200 mL), sonicated for 15 min, and filtered. The solid material was washed with water until the filtrate was neutral (2×100 mL). To increase the purity, the solid material was washed with THF (50+25 mL) and acetonitrile (3×50 mL). The product was dried under vacuum at 40° C.
Yield: 37.15 g (82%), white powder.
Purity: HPLC: 99.9%
Melting point 330° C. (from DSC (peak at 10 K/min))

(C1)

diphenyl(pyren-1-yl)phosphine oxide

Known (CAS 110988-94-8) for long, e.g. from JP 4 876 333 B2, commercially available.

(C2)

(9,10-di(naphthalen-2-yl)anthracen-2-yl)diphenylphosphine oxide

Synthesis According to General Procedure A)

2-bromo-9,10-di(naphth-2-yl)-anthracene: 5.00 g (1.0 eq, 9.81 mmol)

n-butyl lithium, 2.5M in hexane: 4.7 mL (1.2 eq, 11.77 mmol)

THF: 50 mL chlorodiphenylphosphine: 2.1 mL (1.2 eq, 11.77 mmol)

DCM: 60 mL

$H_2O_2$, 30 wt. % in water: 15 mL column chromatography ($SiO_2$, hexane:EE 1:1)

Yield: 3.20 g (52%)

Melting point: none (glassy compound)

ESI-MS: m/z=631 (M+H$^+$)

(C3)

phenyldi(pyren-1-yl)phosphine oxide

Known for long (CAS 721969-93-3), commercially available, e.g. from Luminescence Technology Corp (TW).

[1,1'-binaphthalene]-2,2'-diylbis(diphenylphosphine oxide) (C4)

The well known compound (CAS 86632-33-9) is easily obtainable as an intermediate in the E1 synthesis described above.

Dopants:

lithium quinolin-8-olate

Commercially available lithium 2-(diphenylphosphoryl)phenolate

Synthesis according to patent application WO2013/079678 (compound (1), p. 15-16)

lithium 2-(diphenylphosphoryl)pyridin-3-olate

Synthesis according to patent application EP 2 811 000:

1.1) diphenyl(pyridin-2-yl)phosphine oxide

| 2-fluoropyridine | 2.50 g, 1.0 eq, 25.8 mmol |
| potassium diphenylphosphide | 51.5 mL, 1.0 eq, 25.8 mmol |
| THF | 50 mL |
| DCM | 80 mL |
| hydrogen peroxide, 30 wt. % in water | 25 mL |
| hexane | 20 mL |

Fluoropyridine was dissolved in dry THF. The potassium diphenylphosphide solution was added drop wise during one hour at room temperature. The resulting orange solution was stirred overnight at room temperature. The solvent was removed under reduced pressure and the residue dissolved in dichloromethane. Hydrogen peroxide was added slowly at 0° C. The mixture was stirred overnight at room temperature. The solvent was removed under reduced pressure and the residue treated with hexane. The resulting solid was filtered off, washed with hexane and dried in vacuum.

Yield: 2.2 g (31%), HPLC-MS purity 98.0%.

1.2) (3-hydroxypyridin-2-yl)diphenylphosphine oxide

| diphenyl(pyridin-2-yl)phosphine oxide | 2.0 g, 1.0 eq., 7.2 mmol |
| 2-isopropoxy-4,4,5,5-tetramethyl-1,3,2-dioxaborolane | 4.35 mL, 3.0 eq., 21.5 mmol |
| lithium diisopropylamide | 9.56 mL, 2.0 eq., 14.3 mmol |
| THF | 50 mL |
| Chloroform | 50 mL |
| hydrogen peroxide, 30 wt. % in water | 10 mL |
| DCM | 15 mL |

The starting material was dissolved in dry THF and cooled to −78° C. The borolane was added and the mixture stirred for 20 min. The LDA solution was added dropwise and the temperature was allowed to rise slowly to room temperature. The reaction was stirred for 3 days at room temperature. The solvent was removed under reduced pressure and the residue was dissolved in chloroform. Hydrogen peroxide was added slowly at 0° C. and the mixture was stirred overnight at room temperature. The mixture was extracted with chloroform and brine. The organic phase was dried over magnesium sulphate and the solvent removed under reduced pressure. The residue was dissolved in DCM and precipitated with hexane. The solid was filtered off, washed with hexane and dried in vacuum.

Yield: 1.4 g (67%), GCMS purity 100%, structure confirmed by $^1$H-NMR, $\square$ (ppm)=11.48 (s, 1H, OH), 8.25 (d X from ABX system, J=4.5 Hz, 1H), 7.90 (dd, J=12 Hz and 7.5 Hz, 4H), 7.58 (br t, J=7 Hz, 2H), 7.50 (td, J=7.5 Hz and 3 Hz, 4H), 7.30 (ddd, B from ABX system, 1H), 7.24 (br dd, A from ABX system, 1H).

1.3) lithium 2-(diphenylphosphoryl)pyridin-3-olate
D3

| (3-hydroxypyridin-2-yl)diphenylphosphine oxide | 1.0 g, 1.0 eq., 3.4 mmol |
| lithium tert-butoxide | 0.27 g, 1.0 eq., 3.4 mmol |
| acetonitrile | 40 mL |

The starting material was suspended in dry acetonitrile. Lithium tert-butoxide was added at room temperature and the mixture was heated at reflux for 13 hours. The solid was filtered off, washed with acetonitrile and dried in vacuum.

Yield: 0.865 g (87%), TGA-DSC: m.p. 442° C.

Analytical Data (after Sublimation):

TGA-DSC: mp 445° C.

Elemental analysis: 67.6% C-content (theor. 67.79%), 4.48% H-content (theor. 4.35%),

4.64% N-content (theor. 4.65%)

Device Examples

Auxiliary materials used in device examples not explained above

N3,N3'-di([1,1'-biphenyl]-4-yl)-N3,N3'-dimesityl-[1,1'-biphenyl]-3,3'-diamine, described in WO2014/060526, F1 biphenyl-4-yl(9,9-diphenyl-9H-fluoren-2-yl)-[4-(9-phenyl-9H-carbazol-3-yl)phenyl]-amine, CAS 1242056-42-3, F2

1-(4-(10-(([1,1'-biphenyl]-4-yl)anthracen-9-yl)phenyl)-2-ethyl-1H-benzo[d]imidazole, CAS 1254961-38-0, F3

All data shown here are typical examples. The data in table 1 are medians over typically 16 identical diodes, which are described in the following examples.

Example 1

Bottom emission blue emitting OLED was made by depositing a 10 nm layer of HTML doped with PD2 (matrix to dopant weight ratio of 92:8 wt. %) onto a 90 nm thick ITO-glass substrate (ITO serves as an anode), followed by an 120 nm undoped layer of HTML. Subsequently, a blue fluorescent emitting layer of ABH113 (Sun Fine Chemicals) doped with NUBD370 (Sun Fine Chemicals) (97:3 wt %) was deposited with a thickness of 20 nm. A 36 nm layer of the tested inventive or comparative compound was deposited on the emitting layer together with 50 wt. % D1 or D2 as ETL. Subsequently a layer of aluminium with a thickness of 100 nm was deposited as a cathode.

The observed voltages and quantum efficiencies at the current density 10 mA/cm² are reported in the Table 1.

Figure 3:
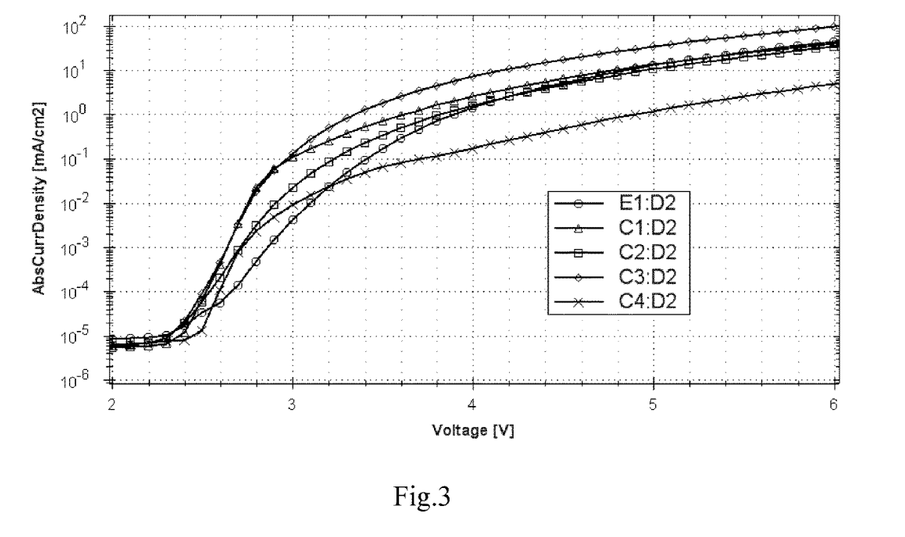
FIG. 3 shows the current density versus applied bias for the inventive semiconducting material E1+D2 and comparative materials C1+D2, C2+D2, C3+D2 and C4+D2 in example 1.
Figure 4:
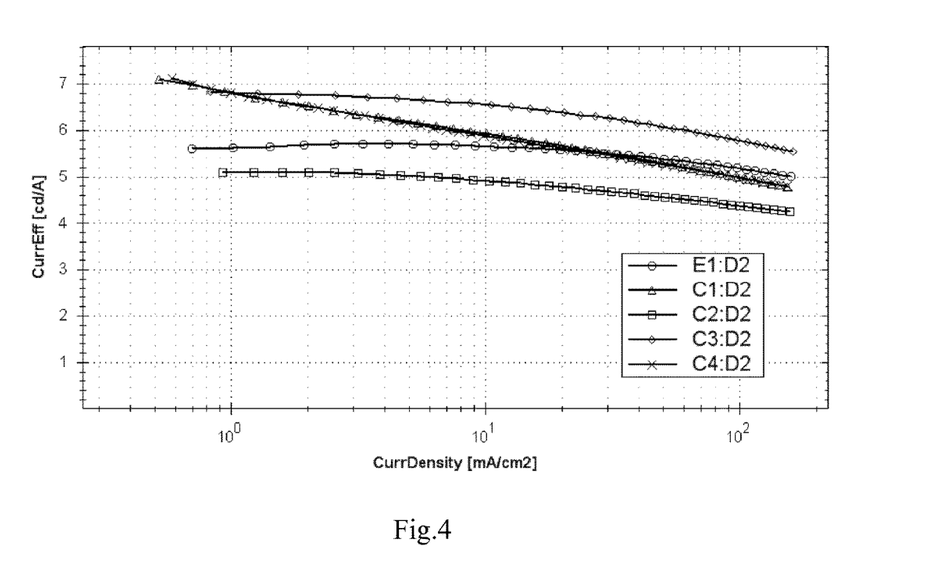
FIG. 4 shows the current efficiency versus current density for the inventive semiconducting material E1+D2 and comparative materials C1+D2, C2+D2, C3+D2 and C4+D2 in example 1.

FIG. 3 and FIG. 4 depict OLED performance curves of devices comprising as electron transporting matrices compounds E1 or C1-C4, respectively. The phosphepine matrix compound E1 performs equally well as the state-of-the-art matrices C1-C2, and markedly better than its closest acyclic analogue C4 lacking the phosphepine ring. Compound C3 that gave experimental devices with slightly better operational voltage and efficiency as E1, in parallel shortened three times the device lifetime. As shows the Table 1, even much more dramatic difference in the lifetime was observed in devices wherein E1 was replaced with its closest acyclic analogue C4, because this comparative compound caused very quick change of initial luminance and voltage in the operating devices.

All the data underline the unexpected beneficial effect of introducing a phosphepine unit into known triaryl phosphine oxide electron transport materials.

Example 2 (Use as a Matrix for Metal-Doped Pn-Junction in a Tandem White OLED)

On an ITO substrate, following layers were deposited by vacuum thermal evaporation:

10 nm thick HTL consisting of 92 wt. % auxiliary material F2 doped with 8 wt. % PD2, 135 nm thick layer of neat F2, 25 nm thick blue emitting layer ABH113 (Sun Fine Chemicals) doped with NUBD370 (Sun Fine Chemicals) (97:3 wt. %), 20 nm thick layer ABH036 (Sun Fine Chemicals), 10 nm thick CGL consisting of 95 wt. % inventive compound E1 doped with 5 wt. % Yb, 10 nm thick HTL consisting of 90 wt. % auxiliary material F2 doped with 10 wt. % PD2, 30 nm thick layer of neat F2, 15 nm thick layer of neat F1, 30 nm thick proprietary phosphorescent yellow emitting layer, 35 nm thick ETL of auxiliary material F3, 1 nm thick LiF layer and aluminium cathode. The diode operated at 6.71 V had EQE 23.7%.

The features disclosed in the foregoing description, in the claims and in the accompanying drawings may both separately and in any combination be material for realizing the invention in diverse forms thereof.

USED ACRONYMS AND ABBREVIATIONS

CV cyclic voltammetry
CGL charge generating layer
DCM dichloromethane
DSC differential scanning calorimetry
DFT density functional theory
DME 1,2-dimethoxyethane
EE ethylester (ethyl acetate)
ETL electron transporting layer
EQE external quantum efficiency of electroluminescence
Fc⁺/Fc ferrocenium/ferrocene reference system
HPLC high performance liquid chromatography
HOMO highest occupied molecular orbital
HTL hole transporting layer
LUMO lowest unoccupied molecular orbital
NMR nuclear magnetic resonance
SPS solvent purification system
TGA thermogravimetry thermal analysis
THF tetrahydrofuran
TLC thin layer chromatography
UV UV/Vis spectroscopy
eq chemical equivalent
mol. % molar percent
wt. % weight (mass) percent
mp melting point
n.a. not applicable
OLED organic light emitting diode
ITO indium tin oxide

The invention claimed is:

1. A semiconducting material comprising:
   at least one matrix compound, wherein the matrix compound comprises at least one phosphepine ring.

2. The semiconducting material according to claim 1, wherein the matrix compound further comprises a dopant.

3. The semiconducting material according to claim 2, wherein the dopant is a metal, a metal salt or a metal complex.

4. The semiconducting material according to claim 3, wherein the metal complex has formula (II):

wherein $A^1$ is a $C_6$-$C_{30}$ arylene or $C_2$-$C_{30}$ heteroarylene comprising at least one atom selected from O, S or N in an aromatic ring, and each of $A^2$-$A^3$ is independently selected from a $C_6$-$C_{30}$ aryl or $C_2$-$C_{30}$ heteroaryl comprising at least one atom selected from O, S, or N in an aromatic ring.

5. The semiconducting material according to claim 4, wherein in formula (II), $A^1$ is phenylene, and/or the substituents $A^2$ and $A^3$ are selected from phenyl or pyridyl.

6. The semiconducting material according to claim 3, wherein the dopant is the metal complex, and the metal complex is a compound comprising at least one ligand attached to a metal atom through at least one oxygen atom and through at least one nitrogen atom; and the metal atom, oxygen atom, and nitrogen atom are members of a 5-, 6-, or 7-membered ring.

7. The semiconducting material according to claim 6, wherein the ligand is an 8-hydroxyquinolinolato ligand.

8. The semiconducting material according to claim 2, wherein the dopant is an electrical dopant.

9. The semiconducting material according to claim 8, wherein the electrical dopant is an n-dopant.

10. The semiconducting material according to claim 1, wherein the phosphepine ring is a phosphepine-1-oxide ring.

11. The semiconducting material according to claim 10, wherein the phosphepine compound has formula (I):

wherein $R^1$, $R^2$ and $R^3$ are independently selected from $C_1$-$C_{30}$-alkyl, $C_3$-$C_{30}$ cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, or $C_6$-$C_{30}$-aryloxy, wherein at least two of the substituents $R^1$, $R^2$, and $R^3$ are linked together in a manner forming at least part of the phosphepine ring.

12. An electronic device comprising: a cathode, an anode, and the semiconducting material according to claim 1, wherein the semiconducting material is arranged between the cathode and the anode.

13. The electronic device according to claim 12, wherein the device further comprises at least one of an electron transporting layer or an electron injecting layer, and the semiconducting material is present in at least one of the electron transporting layer or the electron injecting layer.

14. The electronic device according to claim 13, wherein the device is a light emitting device.

* * * * *